(12) United States Patent
Tan

(10) Patent No.: US 6,471,963 B1
(45) Date of Patent: Oct. 29, 2002

(54) PURIFIED ANTIGENIC MATERIAL AND ITS USE IN THE DIAGNOSIS AND TREATMENT OF DIABETES

(75) Inventor: Kim Sze Tan, Guildford (GB)

(73) Assignee: KS Biomedix Ltd., Esher (GB)

( * ) Notice: Subject to any disclaimer, the term of this patent is extended or adjusted under 35 U.S.C. 154(b) by 0 days.

(21) Appl. No.: 08/452,495

(22) Filed: May 30, 1995

Related U.S. Application Data

(63) Continuation of application No. 08/110,511, filed on Aug. 23, 1993, now abandoned, which is a continuation-in-part of application No. 07/556,125, filed as application No. PCT/GB89/00138 on Feb. 15, 1989, now abandoned.

(30) Foreign Application Priority Data

Feb. 18, 1988 (GB) ................................ 8803756
Feb. 18, 1988 (GB) ................................ 8803757

(51) Int. Cl.[7] ................... A61K 39/00; A61K 39/38; A61K 39/385; A61K 35/55
(52) U.S. Cl. .................. 424/184.1; 424/193.1; 424/562; 514/2; 514/8; 514/21; 514/866
(58) Field of Search .................. 424/131.1, 184.1; 514/3, 866, 2, 8, 21; 350/350, 403, 806, 387.2

(56) References Cited

PUBLICATIONS

Uchigata et al, J. Exp. Med., vol. 165, pp. 124–139, (Jan. 1987).*
Campbell et al, Lab. techniques in Biochemistry, Mol. Biol., Chap. 10 (1984), pp. 186–231.*
Baekkeskov et al J. Clin Invest. 79 926–934 (1987).*
Baekkeskov et al Nature 347 151–156 (1990).*
Baekkeskov et al Nature 298 167–169 (1982).*

* cited by examiner

Primary Examiner—Jyothsna Venkat
Assistant Examiner—Tomas Friend
(74) Attorney, Agent, or Firm—Oliff & Berridge, PLC

(57) ABSTRACT

Islet cell membrane antigen has been purified and, since it displaces islet cell surface antibodies, is of utility in the prevention or treatment of diabetes.

3 Claims, No Drawings

PURIFIED ANTIGENIC MATERIAL AND ITS USE IN THE DIAGNOSIS AND TREATMENT OF DIABETES

RELATION TO EARLIER INVENTION

This is a Continuation of Application Ser. No. 08/110,511 filed Aug. 23, 1993, now abandoned, which is a Continuation-in-Part of Application Ser. No. 07/556,125 filed Jul. 20, 1990 abandoned, which is a 371 of PCT/GB89/00138 filed Jul. 15, 1989.

FIELD OF THE INVENTION

This invention relates to purified antigenic material for use in the prevention and treatment of diabetes.

BACKGROUND OF THE INVENTION

Autoantibodies which are produced by B lymphocytes are involved in the pathogenesis of a number of autoimmune diseases, such as thyroiditis or diabetes, which involve organs such as the thyroid, pancreatic islets or adrenal glands. Some autoantibodies bind cell membrane receptors (or antigens) and trigger an immune response which leads to destruction of the cell or antigen. What triggers the autoimmune response is not known. Autoantibodies can also bind antigens, causing stimulation or blockage of biological processes. The circulating levels of antoantibodies in the body may be low, but such autoantibodies are highly potent and have to neutralized to prevent damage to organs and cells.

Current evidence suggest that Type 1 diabetes mellitus is a chronic autoimmune disease involving two types of islet cell antibodies: (i) islet cell cytoplasmic antibodies (ICCA); (ii) islet cell surface antibodies (ICSA). The ICSA are believed to be central to the initial destruction of the beta cells, whereas ICCA is secondary to the damage. ICSA have been detect in 40–60% of recent-onset diabetics and are present in susceptible individuals long before clinical onset. As such, they may be used as an early predictor of diabetes and as a marker of the silent, ongoing beta cell damage in prediabetic individuals.

Baekkesov et al, *Nature* (London) 298:167–169 (1982), used ICSA-positive sera to search for the autoantigen(s) recognized by ICCA and ICSA. Detailed investigations have been hampered by the small amounts of antibody available and also its polyclonality.

Baekkesov et al have shown that diabetic sera are able to immunoprecipitate surface-labelled islet proteins of 64 kDa and 38 kDa. Hari et al, *Diabetes* 35:517–522 (1986), report a monoclonal antibody from the NOD mouse which recognizes a 64 kDa pancreatic protein. Similarly, Uchigata et al produced a monoclonal antibody from the BB rat which recognizes a 60 kDa and a 68 kDa glycoprotein. Their antibody bound RINm5F cells and frozen pancreas after neuraminidase treatment, suggesting that the antigen is normally hidden by sialic acid residues. Their antibody also reacted with a crude glycolipid extract (only after neuraminidase treatment) which they believe was contaminated with glycoproteins; however, their antibody bound a sequence in the glycolipid paragloboside.

Nayak et al, *Diabetes* 34:617–619 (1985), showed that the autoantigen recognized by diabetic sera has the properties of sialic acid-containing glycolipid. In contrast of Uchigata's monoclonal antibody, they noticed a loss of antibody-binding after neuraminidase treatment. Using preparative thin-layer chromatography of pancreatic glycolipids, they found that the upper-phase polar lipids were able to block the binding of diabetic sera to pancreatic secretions.

Various approaches have been adopted to neutralize autoantibodies, including the use of immunosuppressants, e.g. cyclosporin, and of mouse monoclonal anti-idiotypic antibody neutralization techniques, but neither has been very successful. Immunosuppressants are too non-specific and will attack all B and T cells, while the use of mouse monoclonal anti-idiotypic antibodies often result in the production of human anti-mouse antibodies in patients, considerably reducing the effectiveness of treatment.

Prior to 1998, attempts at producing autoimmune human monoclonal antibodies to islet-cell antigens from type-1 diabetics appear to have been in vain. Co-workers and I have produced numerous human monoclonal antibody-secreting lines, none of which reacts with pancreas, let alone the elusive islet-cell surface antigen.

SUMMARY OF THE INVENTION

The present invention is based on the ability to purify islet cell membrane antigen (ICMA), from cell lines that express the antigen, and the discovery that the ICMA binds ICSA. Therefore, ICMA can be used to neutralize circulating antibodies and to target the B lymphocytes producing the autoantibodies.

Problems of the prior art, i.e. the problems associated with animal models and human autoimmune monoclonal antibody production have been overcome, by obtaining representative antibodies to the islet-cell surface antigen(s) through monoclonal anti-idiotypic antibodies.

DETAILED DESCRIPTION OF THE INVENTION

As indicated above, an anti-idiotypic monoclonal antibody strategy has been used. Assuming the patients' autoimmune antibody constituted a classic Ab1, on immunization both Ab2 and Ab3 should be produced; the latter would be expected to recognize the same antigen(s) as the patient's Ab1 . 137 hybridomas derived from a standard fusion were screened against a library of antigens on a nitrocellulose dot blot system. Ten lines were found to bind only RINm5 cell membranes (of these, 9 secreted IgM).

Preliminary data have shown that two of these antibodies strongly bind islet cells in paraffin sections of human pancreas using an immunoperoxidase system. These antibodies were also able to displace binding of diabetic serum by 50% in an enzyme-linked immunoassay used to detect islet cell membrane auto-antibodies. One of these antibodies was also able to fix complement on living RINm5 cells, suggesting that an external component of the cell membrane was recognized. These results provide evidence that monoclonal anti (anti-idiotypic)(Ab3) antibodies to islet cell surface membrane antigens have been produced.

More specifically, the present invention is based on the generation of a panel of anti-(anti-idiotypic) (Ab3) monoclonal antibodies derived from immunizing tolerant mice with polyclonal human diabetic immunoglobulins (Ab1) from a patient with high levels of ICSA.

The initial screen for the anti-(anti-idiotypic) antibodies involved a nitrocellulose dot-blot system in which 1 μg protein from RINm5 cell membranes was applied to the paper. Positive lines were subcloned and their ability to displace diabetic serum from binding RINm5F membranes in an enzyme-linked immunosorbent assay investigated. One line 55D2 was found to be able to displace the original patient's serum (Ab1) and also other newly-diagnosed diabetic patients' sera by up to 50%. This antibody was coupled to an affinity column to which solubilized RINm5F cell membranes were applied. The eluted fractions were checked on nitrocellulose with the original antibody and positive fractions run on a 5–15% (w/v) SDS/polyacrylamide gel. This revealed that a 64 kDa protein had eluted from the column.

Binding of the antibody 55D2 is not altered by neuraminidase treatment of solubilized RINm5F cell membranes. The antibody recognizes a protein bound by a lectin column derived from *Erythrina crystagalli* which recognizes D-galactose and D-galactoside groups.

Interestingly, while investigating species specificities of the antibody using human, porcine, bovine and rat pancreas, and also the rat insulinoma cell line RINm5F, it was found that even when 100 μg protein was applied to the nitrocellulose no antibody binding was observed, yet routinely 1 μg of protein from RINm5F membranes or 30 ng of the protein eluted from the *Erythrina* column was strongly positive. The antigen appears to be a relatively minor component of the membrane and it is not surprising therefore that there has been a failure to detect cross-reactivity with homogenates of other tissues.

The ability to obtain essentially pure ICMA not only provides the potential for its therapeutic and diagnostic use, but also allows its sequencing and cloning. Further, the ICMA can be digested, e.g. by a variety of enzymes or by chemical treatment, to give an epitope having a lower molecular weight, without loss of activity.

Epitopes containing the sequences specific for locking autoantibodies can be identified by standard gene-sequencing techniques. Once the amino-acid sequence is known, the peptide fragments may be synthetically produced. Synthetic production, e.g. by recombinant technology, may be the preferred route for epitopes that are composed of amino-acids only. However, for epitopes which are glycoproteins, lipoproteins or glycolipids, synthesis is less easy. The preferred route to produce such antigenic determinants is from hybrid cell lines.

Enzyme digestion or chemical treatment of antigens can be carried out to produce individual epitopes which are able to bind specifically to the autoantibodies, so causing a neutralizing effect.

ICMA or epitopes of the invention are essentially free of naturally-associated material. They may be purified by standard techniques. Examples of such techniques are affinity purification, HPLC and electrophoresis.

ICMA or epitope of the invention may be incorporated into a composition which can be used to treat diabetic patients.

Long-term treatment of diabetes may involve not only the neutralization but also the destruction of the B lymphocytes which secrete autoantibodies. ICMA or epitopes of the invention can be tagged with radioactive tracers such as iodine or cytotoxic drugs which can then be used to target and destroy autoantibody-secreting B lymphocytes.

Tagging may be a particular value in the prevention or prophylaxis of diabetes, where it is believed that antoantibodies can be detected 5 to 7 years before the patient becomes insulin-dependent; there may therefore be adequate time for individuals to be treated with neutralizing agents such as ICMA or epitopes specific for the autoantibody, up to the stage when 50% (or more) of the pancreas has been destroyed.

ICMA or its epitopes may also be used to screen biological samples from individuals before an autoimmune disease is manifested. For screening, the epitopes may be incorporated into diagnostic kits.

By the procedure of the following illustrative Example, islet cell membrane antigens (ICMA) have been purified from cell lines that express the antigen and have demonstrated binding of the ICMA with human islet cell autoantibodies (ICA).

EXAMPLE

An anti-anti-idiotypic mouse monoclonal antibody (see above) was used for the purification of the ICMA. 5 mg purified monoclonal antibodies were coupled on to 1 g activated beads (Guildhay). The column was washed 3 times with phosphate-buffered saline (PBS), and a solubilized islet cell membrane preparation, passed through a 0.2 μm filter (Millipore), was applied to the column. The column was then washed with PBS until there was no protein in the eluate. Bound ICMA was eluted at 4° C., and fractions containing ICMA were pooled and dialyzed against PBS.

The purified ICMA was characterized in the following ways:

(a) Nitrocellulose blotting: Purified ICMA was spotted on to nitrocellulose membranes, incubated with ICSA-positive diabetic sera and anti-anti-idiotypic MAb. Staining was visualized by Coomassie Blue.

(b) Enzyme-linked immunosorbent assay (ELISA): Purified ICMA was coated on to sensitized microtiter wells, incubated with ICSA-positive diabetic sera and anti-anti-idiotypic MAb. Binding was visualized by adding either anti-human-HRP or anti-Mouse-HRP conjugate; see *Tan et al, Diabetes* 37:204 (1988).

(c) Displacement ELISA: The purified ICMA will displace binding of ICSA-positive diabetic sera in the ICSA EIA kit available from Guildhay Antisera Ltd., Guildford, UK).

(d) SDS-gel Electrophoresis: By classical SDS polyacrylamide gel electrophoresis, the ICMA appeared as a single band with a molecular weight of 60,000–65,000 Daltons.

(e) Nature: The ICMA is apparently a glycoprotein with sialic acid terminal groups. Neuraminidase treatment, however, did not affect the binding of the ICMA to ICSA-positive diabetic sera.

Because it is believed that circulating ICSA initiates beta cell damage when bound to ICMA, it is possible to use complementary peptides such as epitopes or chemicals to bind the ICMA and thus prevent ICSA binding. In this way, the beta cells could effectively be prevented from damage. The design of these "protective" peptides or chemical compounds follows from knowledge of the amino-acid sequence of the antigenic site of ICMA.

Further, an enzyme-linked immunosorbent assay (EIA) for ICSA has been developed, using membrane antigens from the rat insulin-secreting RINm5F cell-line. These studies investigate the relative frequencies of islet cell surface and cytoplasmic antibodies in sera of diabetics. Serum samples from 30 recently-diagnosed (6 months) Type 1 diabetic patients, and 20 healthy non-diabetic controls were screened for ICSA by the EIA and a cell-surface immunoradiometric assay (IRMA). The samples were also assayed for ICCA by indirect immunofluorescence staining, as described by Bottazzo & Gleichmann (1986).

The ICSA cell-IRMA detected RIN5mF cell surface-bound immunoglobulins. Serum samples (final dilution 1/20) were incubated with $10^4$ viable cells in polystyrene tubes (6 minutes, 37° C.) in 200 μl phosphate-buffered saline (PBS) + 0.5% bovine serum albumin (BSA). Cells were washed with 1 ml PBS +0.5% BSA and centrifugation (200 g, 10 min), resuspended in 200 $\mu$l $^{125}$I-sheep anti-human IgG (100,00 cpm/tube), and incubated for 60 min at 37° C. After washing, bound radioactivity was determined using a gamma counter.

RIN5mF plasma membranes (prepared by differential centrifugation) were solubilized in PBS containing 1% Triton X-100. Membrane antigens were coated onto microtiter wells (1 $\mu$g protein/well). 200 $\mu$l serum samples, diluted 1/20 were incubated (30 minutes, 37° C.) in microtiter wells. Wells were washed with PBS+0.1% (w/v) gelatin+0.5% Tween 20 (PBSGT). After incubation with 200 $\mu$l peroxidase-conjugated sheep anti-human IgG (30 minutes, 37° C.), wells were washed with PBSGT. Colour was visualized with 200 $\mu$l substrate (tetramethylbenzidine) and incubated (30 minutes, 37° C.). The reaction was stopped with 50 $\mu$l 2.5 M $H_2SO_4$, and optical density (450 nm) readings made. For each assay, samples were determined positive if mean values exceeded 2 standard deviations of the mean value of a set of 10 negative samples.

Of 30 diabetic patient sera, 12 (40%) were ICSA-positive in the ICSA-ELISA and 13 (43%) were ICSA-positive in the cell-IRMA. 10 samples (33%) were ICCA-positive. The 20 sera from healthy non-diabetic controls were negative in all assays. The preliminary data showed a good correlation between the ICSA-ELISA and the ICSA-cell-IRMA. 12 diabetic samples were positive in both the ICSA-ELISA and the ICSA-cell-IRMA. 17 diabetic samples were negative in both the ISCA-ELISA and ICSA-cell-IRMA. The incidence of ICSA obtained by the IRMA and ELISA is comparable to that obtained in previous studies (32%); see *Lernmark et al* (1978). The relatively low incidence of ICSA in sera of recent-onset diabetic patients may be due to the falling titer of these autoantibodies after destruction of islet cell surface antigens. It is possible that higher levels of ICSA precede beta-cell destruction and the onset of insulin-dependency. The lower correlation between the ICSA-ELISA and the immunofluorescence assay for ICCA indicates that each diabetic sample may have different levels of these two classes of antibodies. Larger studies of the incidence of these antibodies in individuals with increased risk of developing the disease (e.g. first-degree relatives) will assist in determining their predictive significance for Type I diabetes mellitus.

In order to establish that ICMA has an epitope binding ICSA, an affinity-purified ICMA displacement study was conducted. More particularly, affinity-purified antigens from islet cell RINm5F membranes were used in a competition study with an ICSA positive control. It was found that binding in the ELISA was displaced, as shown by the optical density values (at 450 nm) recorded in the following Table.

|                         | Serum Dilution | | |
| --- | --- | --- | --- |
| Affinity-purified ICMA  | 1:10 | 1:50 | 1:500 |
| Without ICSA            | 1.6  | 1.3  | 0.4   |
| After ICSA preincubation| 1.4  | 0.65 | 0.2   |

What is claimed is:

1. A method for the prevention or treatment of diabetes in a human subject, which comprises administering to the subject an effective amount of an essentially pure pancreatic islet cell membrane antigen or epitope thereof that can bind to islet cell surface antibodies (ICSA).

2. The method of claim 1, wherein the antigen has a molecular weight of 60,000–65,000 Daltons as determined by SDS gel electrophoresis.

3. The method of claim 1, wherein the islet cell membrane antigen or epitope thereof is tagged with a radioactive tracer or a cytotoxic drug and is effective to target and destroy autoantibody-secreting B lymphocytes.

* * * * *